United States Patent
Bedingham et al.

(10) Patent No.: US 6,855,553 B1
(45) Date of Patent: Feb. 15, 2005

(54) SAMPLE PROCESSING APPARATUS, METHODS AND SYSTEMS

(75) Inventors: William Bedingham, Woodbury, MN (US); Barry W. Robole, Woodville, WI (US); James Aysta, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 438 days.

(21) Appl. No.: 09/677,805

(22) Filed: Oct. 2, 2000

(51) Int. Cl.[7] .................... G01N 35/00; G01N 1/00; G01N 9/30; B32B 5/02; B01L 11/00
(52) U.S. Cl. .................... 436/45; 436/43; 436/174; 436/177; 422/63; 422/64; 422/72; 422/101
(58) Field of Search .............. 422/101, 63, 64; 436/180, 174, 177, 43, 45

(56) References Cited

U.S. PATENT DOCUMENTS

| | | | |
|---|---|---|---|
| 3,767,364 A | * 10/1973 | Ritchie et al. | ............... 422/50 |
| 3,902,660 A | 9/1975 | Barber | |
| 4,236,894 A | * 12/1980 | Sommervold | ............... 436/43 |
| 4,284,602 A | 8/1981 | Kelton et al. | |
| 5,077,013 A | * 12/1991 | Guigan | ............... 422/64 |
| 5,160,702 A | 11/1992 | Kopf-Sill et al. | |
| 5,219,526 A | * 6/1993 | Long | ............... 422/64 |
| 5,425,918 A | * 6/1995 | Healey et al. | ............... 422/64 |
| 5,489,414 A | * 2/1996 | Schreiber et al. | ............... 422/64 |
| 5,585,069 A | 12/1996 | Zanzucchi et al. | |
| 5,679,309 A | * 10/1997 | Bell | ............... 422/67 |
| 5,698,450 A | * 12/1997 | Ringrose et al. | ............... 436/526 |
| 5,814,276 A | * 9/1998 | Riggs | ............... 422/65 |
| 5,863,708 A | 1/1999 | Zanzucchi et al. | |
| 6,030,581 A | 2/2000 | Virtanen | |
| 6,048,457 A | 4/2000 | Kopaciewicz et al. | |
| 6,063,589 A | 5/2000 | Kellogg et al. | |
| 6,121,054 A | 9/2000 | Lebl | |
| 6,133,045 A | * 10/2000 | Johnson et al. | ............... 436/177 |
| 6,508,984 B1 | * 1/2003 | Turner et al. | ............... 422/65 |
| 2002/0127727 A1 | * 9/2002 | Bach et al. | ............... 436/48 |
| 2003/0017613 A1 | * 1/2003 | Jakubowicz | ............... 436/174 |
| 2003/0026733 A1 | * 2/2003 | LaCourt | ............... 422/64 |
| 2003/0031599 A1 | * 2/2003 | Brown | ............... 422/100 |
| 2003/0040117 A1 | * 2/2003 | Devlin | ............... 436/46 |
| 2003/0044990 A1 | * 3/2003 | Seto | ............... 436/43 |

FOREIGN PATENT DOCUMENTS

| | | |
|---|---|---|
| JP | 63019558 | 1/1988 |
| WO | WO 00/40750 | 7/2000 |

OTHER PUBLICATIONS

T. Maniatis et al., Molecular Cloning, A Laboratory Manula, Cold Spring Harbor Laboratory, Title page, Publication page, and Table of Contents (8 pgs.) (1982).

* cited by examiner

Primary Examiner—Jill Warden
Assistant Examiner—Brian R. Gordon
(74) Attorney, Agent, or Firm—Christopher D. Gram; Robert W. Spraque

(57) ABSTRACT

Apparatus, methods, and systems for processing sample materials that may be presented in a standard microtiter plate are disclosed. The present invention provides a bridge between the standard microtiter plate systems, methods, protocols, etc. with their stationary wells and rotating sample processing devices that allow users to obtain the rapid processing advantages of the newer sample processing devices while retaining the benefits of the standard microtiter plate formats.

38 Claims, 4 Drawing Sheets

SAMPLE PROCESSING APPARATUS, METHODS AND SYSTEMS

FIELD OF THE INVENTION

The present invention relates to sample processing systems and methods. More particularly, the present invention provides apparatus, methods, and systems for processing sample materials.

BACKGROUND

Many different chemical, biochemical, and other reactions are sensitive to temperature variations. The reactions may be enhanced or inhibited based on the temperatures of the materials involved. Although it may be possible to process samples individually and obtain accurate sample-to-sample results, individual processing can be time-consuming and expensive.

Examples of some thermal processes that may be sensitive to temperature variations include, e.g., the manipulation of nucleic acid les to assist in the deciphering of the genetic code. See, e.g., T. Maniatis et al. *Molecular Cloning, A Laboratory Manual*, Cold Spring Harbor Laboratory (1982). Nucleic acid manipulation techniques include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

One approach to reducing the time and cost of thermally processing multiple samples using such techniques is to use a device including multiple chambers in which different portions of one sample or different samples can be processed simultaneously. Although widely accepted standardized systems have been developed using microtiter plates having, e.g., 96, 384 or more wells, to speed the processing of multiple sample, even faster sample processing is still desired.

One disadvantage of such devices is, however, their non-standard format as compare to, e.g., the widely accepted standard microtiter plates. As a result, it may be prohibitive in terms of, e.g., equipment costs, test result acceptance, etc. for a facility to abandon the industry standard processes completely and adopt a new test methodology and new equipment.

Another disadvantage of such an approach is in the limited volume available on such devices, which can make cleanup of reaction products difficult due to the limited storage for cleanup solutions.

SUMMARY OF THE INVENTION

The present invention provides apparatus, methods, and systems for processing sample materials that my presented in a standard microliter plate. More particularly, the present invention provides a bridge between the standard microliter plate systems, methods, protocols, etc. with their stationary wells and rotating sample processing devices that allow users to obtain the rapid processing advantages of the newer sample processing devices while retaining the benefits of the standard microtiter plate formats.

For example, the rotating sample processing devices can be used to rapidly and accurately perform required processing of the sample materials by virtue of their rotation. That rotation may be used to expose the processing chambers to energy and/or to assist in transporting the sample material to different areas on the processing devices.

In addition, cleanup of the processed sample materials can be performed off of the sample processing device, thereby mitigating any concerns regarding available volume of the sample processing device for any cleaning solutions and materials.

A further advantage of the present invention is its amenability to automation to further enhance speed and/or cost of obtaining the desired results.

In one aspect, the present invention provides an apparatus for processing sample materials, the apparatus including a platform having an upper surface and a lower surface; a plurality of stationary fluid chambers opening at the upper surface of the platform; and retention structure occupying a portion of the upper surface of the platform, wherein the retention structure is capable of retaining a rotating multi-chambered processing device proximate the upper surface of the platform.

In another aspect, the present invention provides an apparatus for processing sample materials, the apparatus including a platform having an upper surface and a lower surface; a plurality of stationary fluid chambers opening at the upper surface of the platform; retention structure occupying a portion of the upper surface of the platform; and a processing device located within the retention structure proximate the upper surface of the platform, the processing device including a plurality of process chambers, wherein the processing device is capable of being rotated within the retention structure to move the plurality process chambers.

In another aspect, the present invention provides a method of processing sample material by providing a platform having an upper surface and a lower surface, a plurality of stationary fluid chambers opening at the upper surface of the platform, and retention structure occupying a portion of the upper surface of the platform; providing a processing device in the retention structure proximate the upper surface of the platform, the processing device including a plurality of process chambers; providing sample material in a plurality of the plurality of process chambers on the processing device; delivering energy to the process chambers containing sample material to raise the temperature of the sample materials in the process chambers; and rotating the processing device about an axis of rotation within the retention structure while delivering the energy, wherein the temperature of the sample materials in the process chambers is controlled as the processing device rotates to process the sample materials.

In another aspect, the present invention provides a method of processing sample material by providing a platform having an upper surface and a lower surface, a plurality of stationary fluid chambers opening at the upper surface of the platform, and retention structure occupying a portion of the upper surface of the platform, wherein the plurality of stationary fluid chambers are arranged in a rectilinear array on the upper surface of the platform; placing a processing device in the retention structure proximate the upper surface of the platform, the processing device including a plurality of process chambers; positioning at least one of the process chambers on the processing device at a transfer site proximate the upper surface of the platform, wherein the location of the transfer site is fixed relative to the stationary fluid chambers; loading sample material in a plurality of the plurality of process chambers on the processing device, wherein the process chambers are loaded while positioned at the transfer site; rotating the processing device about an axis of rotation within the retention structure on a spindle extending through a spindle opening formed through the upper and lower surfaces of the platform; delivering energy to at least some of the plurality of process chambers containing sample material while rotating the processing device to control the temperature of the sample materials in the process chambers, whereby the sample materials are processed; and transferring the sample materials from the process chambers on the processing device to the plurality of stationary fluid chambers on the platform after processing the sample materials; wherein the sample materials in the process chambers are transferred while the process chambers are located at the transfer site.

In another aspect, the present invention provides a system for processing sample material, the system including a workspace including a processing station; at least one platform located within the workspace, each platform having an upper surface and a lower surface, a plurality of stationary fluid chambers opening at the upper surface of the platform, and retention structure occupying a portion of the upper surface of the platform; at least one processing device located within the workspace, each processing device including a plurality of process chambers, wherein rotation of the processing device within the retention structure on the platform moves the plurality process chambers in a circular pattern; a spindle located at the processing station; and a transfer device operative within the workspace, the transfer device capable of transferring sample material from the processing station to another location within the workspace.

These and other features and advantages of the present invention are described with respect to illustrative embodiments of the invention presented below.

DETAILED DESCRIPTION OF ILLUSTRATIVE EMBODIMENTS OF THE INVENTION

The present invention provides apparatus, methods, and systems for processing sample materials that may be presented in a standard microtiter plate. More particularly, the present invention provides a bridge between the standard microtiter plate systems, methods, protocols, etc. and rotating sample processing devices.

Figure 1:
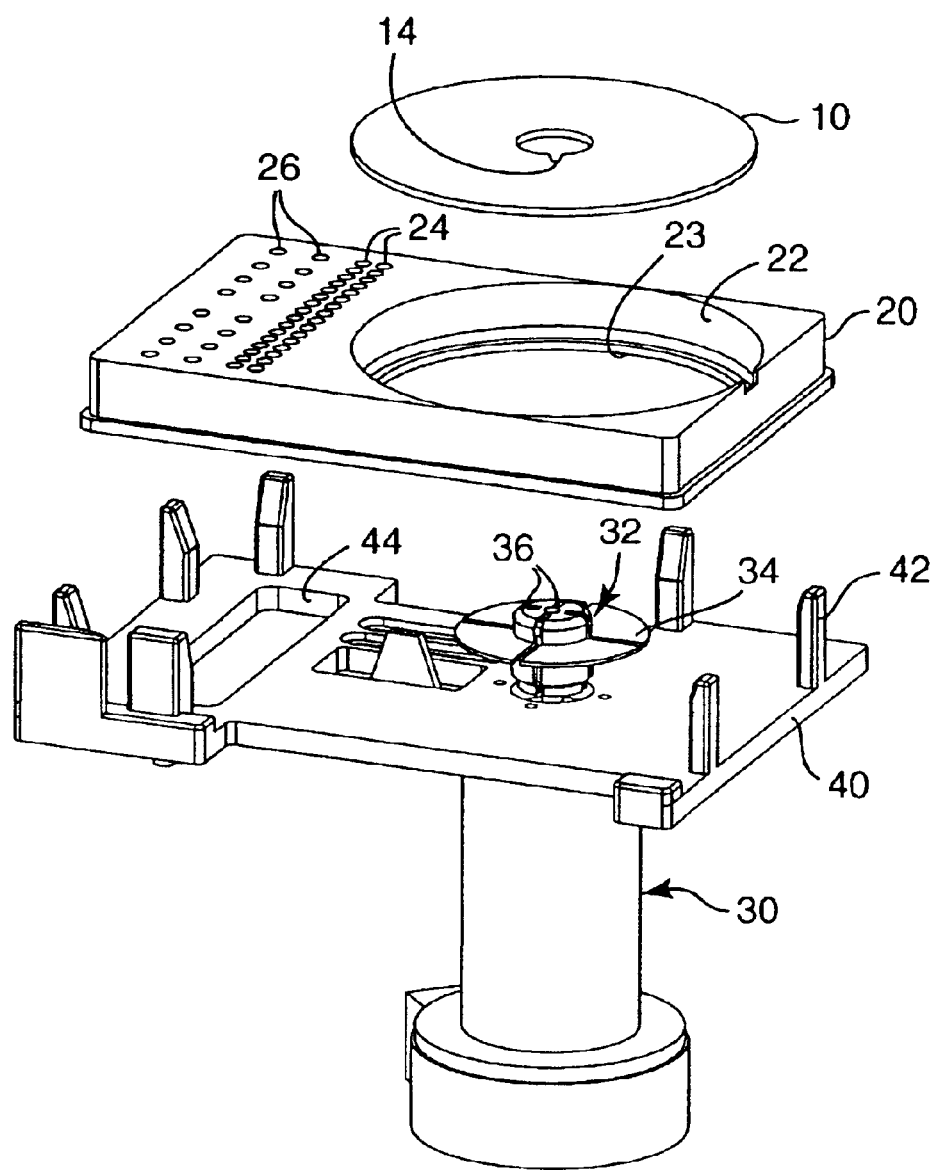
FIG. 1 is an exploded diagram of one platform and sample processing device according to the present invention.
Figure 2:
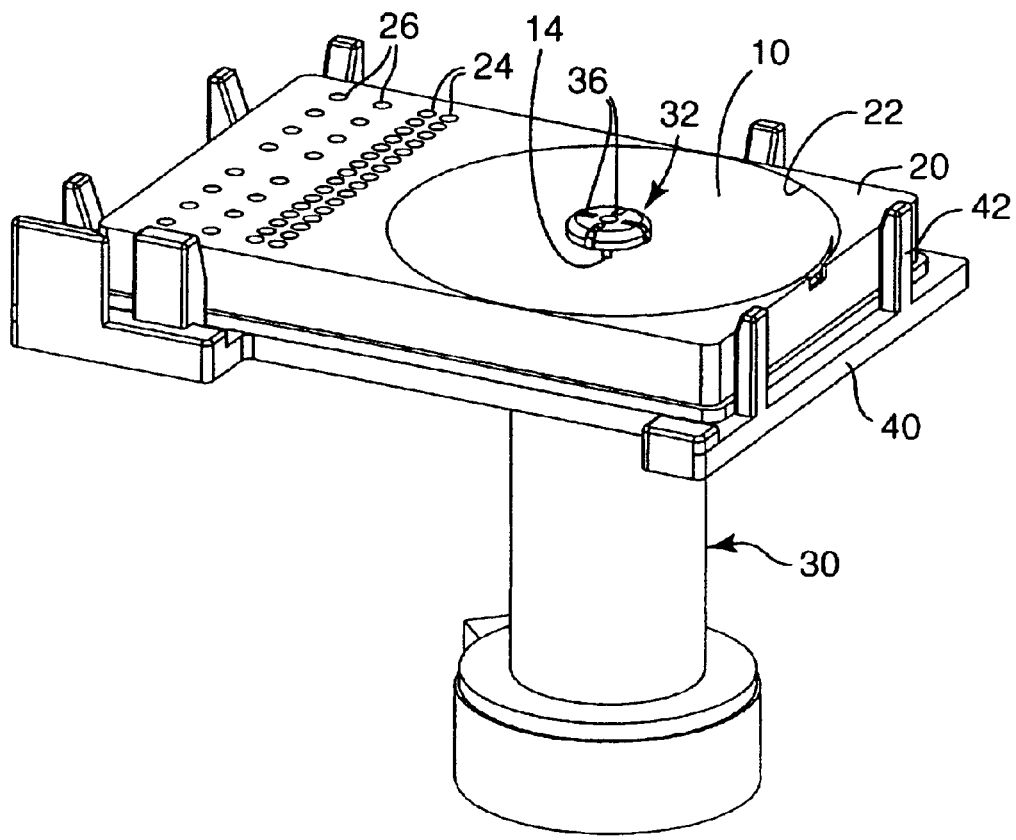
FIG. 2 is an assembled view of the platform and sample processing device of FIG. 1.

A portion of one illustrative system is depicted in FIGS. 1 and 2. The depicted portion of the system includes a sample processing device 10 that may preferably be provided in a disc-shaped format such as that depicted. Examples of suitable disc-shaped devices 10 may be found in, for example, U.S. Provisional Patent Application Ser. No. 60/214,642 filed on Jun. 28, 2000 and titled SAMPLE PROCESSING DEVICES, SYSTEMS AND METHODS and U.S. Provisional Patent Application Ser. No. 60/237,151 filed on even date herewith and titled SAMPLE PROCESSING DEVICES, SYSTEMS AND METHODS. Among the processing devices described in those references, it may be preferable to use those that include features conducive to automated loading and/or unloading as well as automated processing (e.g., tapered inlet ports, seal systems on output chambers, registration systems, etc.). It should further be noted that the devices described in those references may be manufactured according to the principles described in U.S. Provisional Patent Application Ser. No. 60/214,508 filed on Jun. 28, 2000 and titled THERMAL PROCESSING DEVICES AND METHODS.

Other processing devices may also be used in connection with the present invention, although they may preferably be modified to incorporate features conducive to automated loading and/or unloading, as well as automated processing. Examples of some potentially useable rotating processing devices include, but are not limited to those described in, e.g., U.S. Pat. Nos. 5,160,702 (Kopf-Sill et al.); 5,585,069 (Zanzucchi et al.); 6,030,581 (Virtanen); and 6,063,589 (Kellogg et al.) as well as in International Publication No. WO 00/40750 (Orlefors et al.).

A platform 20 is also provided and includes retention structure 22 on its upper surface that is capable of retaining the processing device 10 proximate the upper surface of the platform 20 while the processing device 10 is rotating. The retention structure 22 may preferably be slightly larger than the processing device 10 to allow clearance for the processing device 10 to rotate within the retention structure 22. It may be preferable, but not required, that the retention structure 22 also be in the same general shape as the thermal processing device 10, e.g., circular for disc-shaped processing device 10.

It may be preferred that the retention structure 22 be provided in the form of a cavity as depicted in FIGS. 1 and 2. On one alternative, the retention structure on a platform 20 may be provided in the form of, e.g., a series of raised posts or protrusions that cooperate to retain the processing device 10 within a desired area on the upper surface of the platform 20.

In one variation, the retention structure may allow for placement and removal of a processing device 10, such as the retention structure 22 illustrated in FIGS. 1 and 2. As a result, the platform 20 may be used with multiple processing devices 10 that may be located in and removed from the retention structure as needed. In another alternative, such retention structure may allow the user to select a particular processing device 10 for use with the platform 20.

In another variation, the retention structure may be used to retain a captive processing device 10 within a specified area on the upper surface of the platform 20. As used in connection with the present invention, a "captive" processing device means that the processing device cannot be top-loaded into the retention structure without removing a portion of the platform 20 or somehow distorting the shape of the processing device 10. A captive processing device would be retained within the retention structure even if the platform 20 were oriented such that the upper surface faced the ground.

The depicted platform 20 also includes optional sample fluid chambers 24 that may be used as a staging area for sample materials to be introduced onto the processing device 10. The fluid chambers 24 may also contain one or more reagents that may be used on the processing device 10. The fluid chambers 24 may preferably be arranged in a rectilinear array that is similar in form to arrays of wells found on a standard microtiter plate having, e.g., 96, 384, or more wells.

Figure 3:
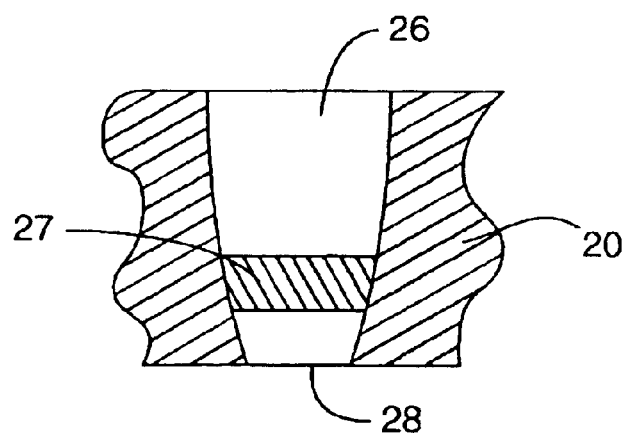
FIG. 3 is an enlarged cross-sectional view of one fluid chamber on the platform including filter material.

The platform 20 also includes fluid chambers 26 to be used to receive processed sample material removed from the processing device 10. The fluid chambers 26 may include filter material 27 within the chamber 26 (see FIG. 3). The fluid chambers 26 may also include a drain port 28 opening at the lower surface of the platform 20 such that sample material introduced into the chamber 26 may pass through the fluid chamber 26. If filter material 27 is present within the chamber 26, then the sample material is filtered during its passage through the chamber 26.

The fluid chambers 26 on the platform 20 may preferably be arranged in a rectilinear array that is similar in form to arrays of wells found on standard microtiter plates. Further, the fluid chambers 26 are also preferably spaced at intervals compatible with a standard microtiter plate such that wells on a standard microtiter plate located beneath the platform 20 would be aligned with any drain ports of the output wells 26. As a result, processed sample materials removed from the device 10 and transferred to the fluid chambers 26 could be passed through the drain ports of the fluid chambers 26 and into the wells on a standard microtiter plate for additional processing using conventional equipment and procedures.

Also depicted in FIGS. 1 and 2 is a support carriage 40 including alignment structure 42 for receiving the platform 20. The support carriage 40 may preferably include an opening 44 to allow for passage of processed sample materials from the fluid chambers 26 to a standard microtiter plate located beneath the support carriage 40. The alignment structure 42 may include sloped surfaces as depicted to assist in guiding the platform 20 into position on the support carriage 40.

A spindle 30 is also depicted in FIGS. 1 and 2 that can be used to rotate the processing device 10 to facilitate processing of the sample materials located thereon. The spindle 30 preferably extends upward through the support carriage 40 and through a spindle opening 23 in the retention structure 22 of the platform 20 (when the plate 20 is located on the carriage 40).

A chuck 32 adapted to mate with the processing device 10 is preferably provided on the end of the spindle 30. The chuck 32 preferably includes a support plate 34 adapted to support the device 10 and at least one, preferably multiple, locking arms 36 in the form of levers that swing outward to retain the device 10 on the chuck 32 as the spindle 30 rotates. The arms 36 may preferably be weighted (or otherwise constructed) such that when the spindle 30 is not rotating, the arms 36 are retracted to allow for placement and removal of the device 10 without hindrance from the arms 36.

In the use of the combination of platform 20 and processing device 10, it may be preferred to position a processing chamber on the processing device 10 at a transfer site proximate the upper surface of the platform 20. A "transfer site" as used herein, is a location at a fixed position relative to the stationary fluid chambers 26. It may be preferred that the stationary fluid chambers 26 and the transfer site 25 be positioned according to a common reference system, e.g., on a rectilinear grid, according to polar coordinates, etc. It may further be preferred that all of the sample fluid chambers 24, stationary fluid chambers 26, transfer site 25 and the location at which loading chambers 16 are positioned for loading be defined by a common reference system.

Figure 4:
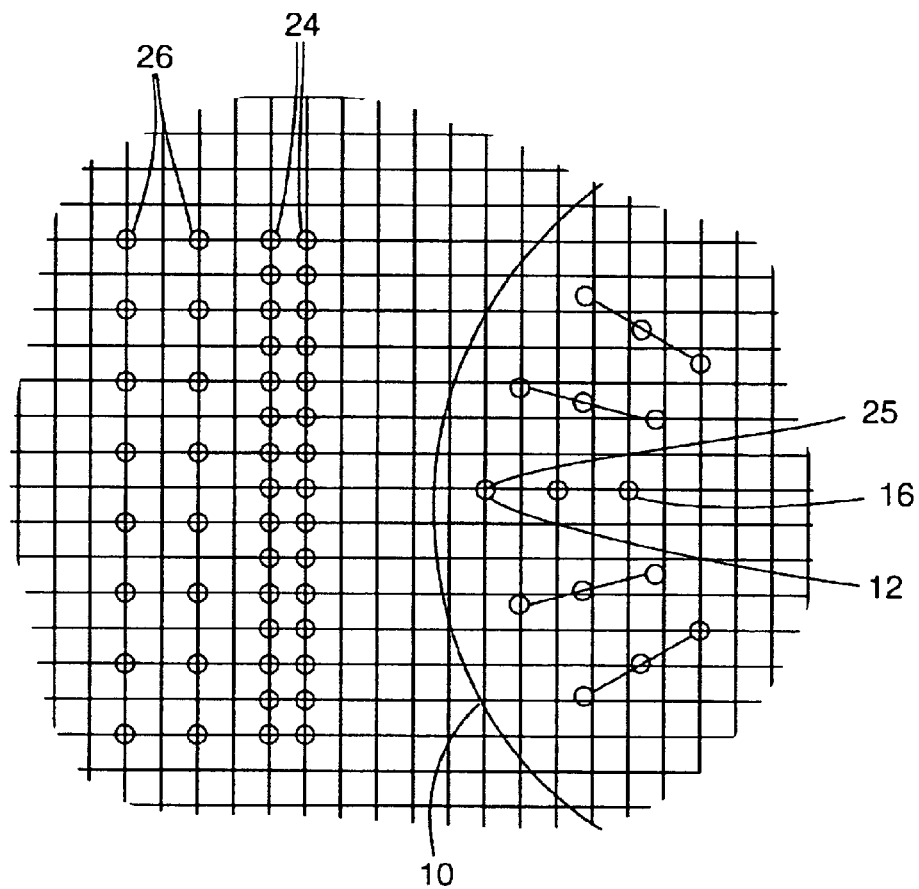
FIG. 4 is a schematic diagram illustrating the positioning of various features of the apparatus on a rectilinear grid.

Referring to FIG. 4, one example of a suitable reference system is depicted in which the stationary fluid chambers 26 are located at intersection points on a rectilinear grid, while the transfer site 25 is located at another of the intersection points on the grid. Because the processing device 10 rotates within the retention structure on the platform, different process chambers 12 on the processing device 10 can be indexed into position at the transfer site 25. It may also be preferred that any sample fluid chambers 24, as well as loading chambers 16 on the processing device 10 be positioned at locations defined by a rectilinear array.

Positioning of the processing device 10 to accomplish, e.g., providing the processing chambers 12 on the processing device 10 at the transfer site 25 may be accomplished by any suitable technique. A variety of registration systems and methods are discussed in, e.g., U.S. Provisional Patent Application Ser. No. 60/214,642 filed on Jun. 28, 2000 and titled SAMPLE PROCESSING DEVICES, SYSTEMS AND METHODS.

One example of a registration system including complementary structures is depicted in FIGS. 1 and 2, where one or more of the arms 36 may cooperate with a keyed slot 14 on the device 10 for registering the rotational position of the processing device 10 on the spindle 30 and, therefore, within the retention structure 22 on the platform 20. Such structure can be used to fix the rotational position of the processing device 10 on the spindle 30, provided for accurate indexing of the processing device 10 to put the various features on the processing device 10 in the desired positions.

The apparatus depicted in FIGS. 1 and 2 may preferably be used in connection with a variety of transfer devices available from a variety of manufacturers including, but not limited to: Beckman Coulter, Inc. (Fullerton, Calif.), Packard Instrument Company (Meriden, Conn.), Tomtec (Hamden, Conn.), MWG-Biotech Inc. (High Point, N.C.), and Qiagen (Valencia, Calif.). Such automated transfer devices typically include pick-and place robotic technology and can be outfitted with a processing station including the support carriage 40 and spindle 30 adapted to receive a platform 20 and associated thermal processing device 10.

Figure 5:
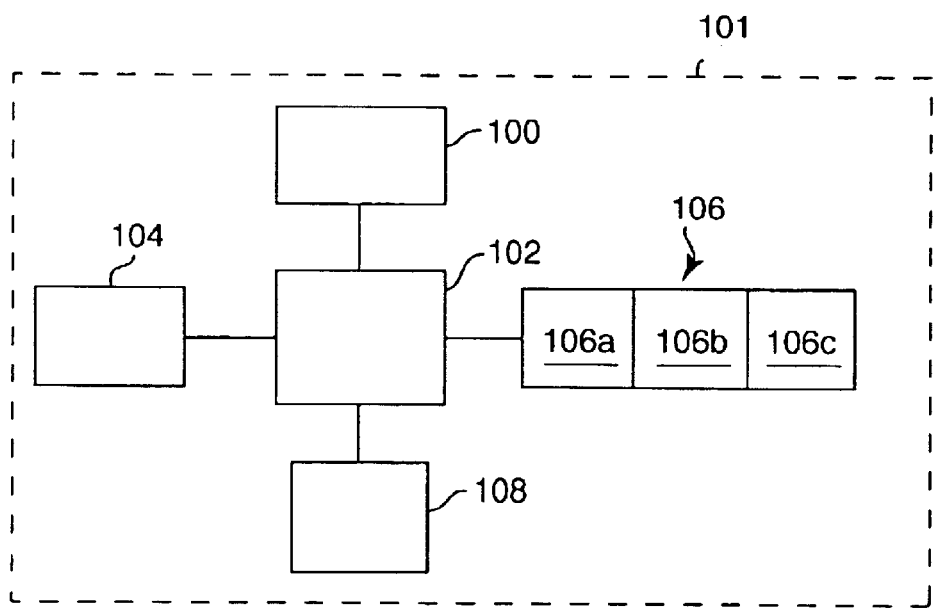
FIG. 5 is a schematic diagram of a system using the platforms and sample processing devices of the present invention.

One such system is depicted in FIG. 5 and includes a controller 100, transfer device 102, supplies 104 (which may include, e.g., platforms, thermal processing devices, pipette tips, cleanup materials, sample materials, etc.), a processing station 106 (including, e.g., a support carriage 106a, spindle 106b, and source of electromagnetic radiation 106c) and an unloading station 108. All of these components may preferably be located within a workspace 101.

In use, the processing station 106 can be loaded with the necessary materials from supplies 104 (e.g., a platform, sample materials, processing device, etc.) using the transfer device 102. Sample materials can then be processed at the processing station 106, with the transfer device 102 being used to transfer sample materials to the desired locations (e.g., from sample fluid chambers on the platform to loading chambers on a processing device and/or from process chambers on the processing device to stationary fluid chambers on the platform, etc.).

After processing at the processing station 106, the platform (with processed sample material) may be moved to, e.g., the unloading station 108 using the transfer device 102, where the processed sample materials may cleaned up using supplies 104 (delivered by the transfer device 102). The sample materials may then be transferred to a standard microtiter plate at the unloading station 108 for further processing of the sample materials.

In some embodiments, it may be preferred to provide the processing station 106 in the form of one of the systems described in, e.g., U.S. Provisional Patent Application Ser. No. 60/214,642 filed on Jun. 28, 2000 and titled SAMPLE PROCESSING DEVICES, SYSTEMS AND METHODS (see, e.g., FIG. 9 and the corresponding description in that application) or U.S. Provisional Patent Application Ser. No. 60/237,151 filed on even date herewith and titled SAMPLE PROCESSING DEVICES, SYSTEMS AND METHODS.

Furthermore, in another variation the platforms of the present invention may be provided with only a retention structure adapted to receive a rotating processing device, i.e., in the absence of any fluid chambers for staging sample materials or receiving processed sample materials from the processing devices. The rectilinear shape of the preferred platforms allows the rotating processing devices to be used in largely conventional robotic transfer devices. In such a system, it may be desirable, e.g., to provide pipettes or other fluid transfer apparatus that include some filtering structure within them to filter the processed sample materials as they are drawn from the processing devices. The filtered sample materials can then be deposited in the wells of, e.g., standard microtiter plates for conventional processing. Examples of some fluid transfer apparatus that may include materials to clean up samples are described in, e.g., U.S. Pat. No. 6,048,457 (Kopaciewicz et al.).

Figure 6:
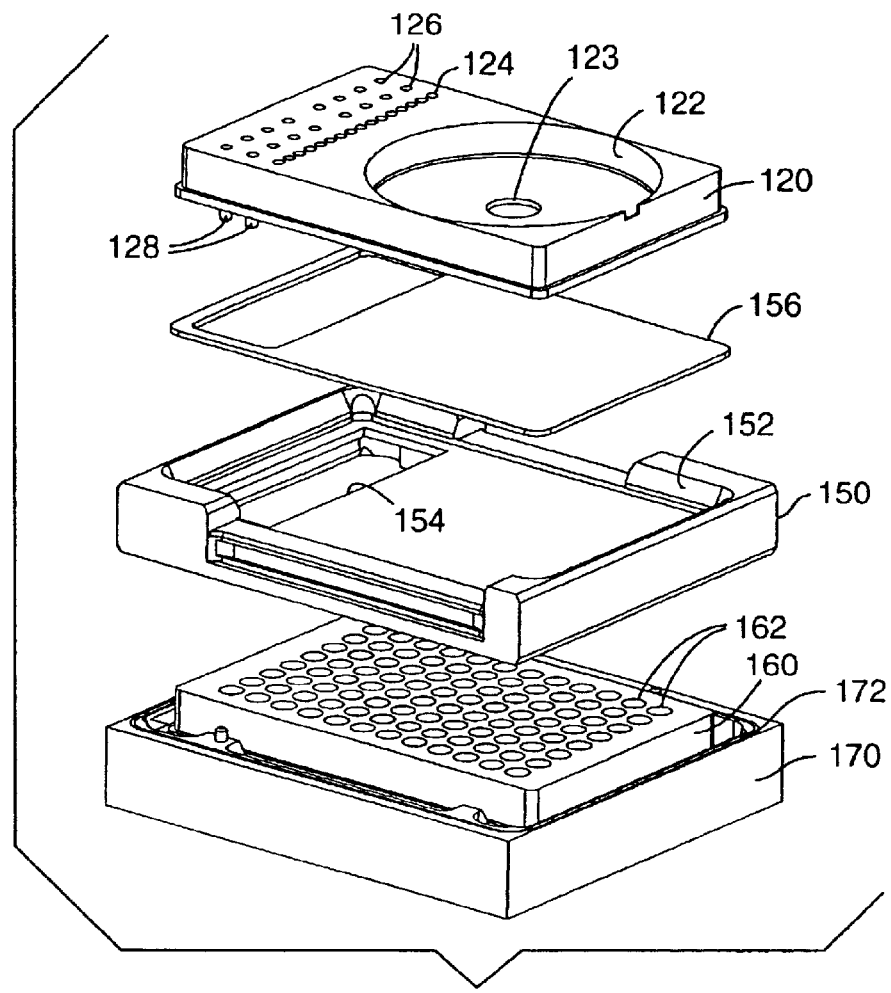
FIG. 6 is an exploded diagram of another platform and sample processing device according to the present invention.
Figure 7:
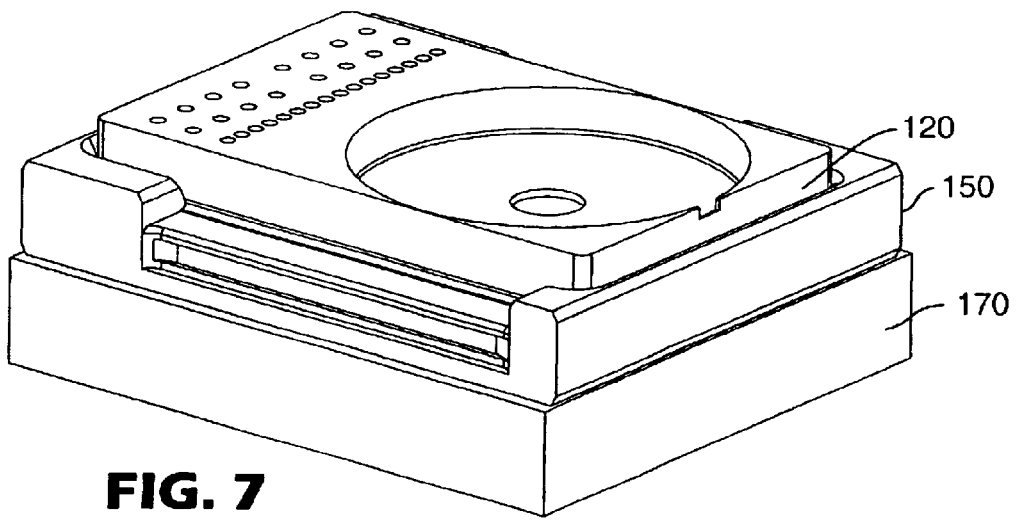
FIG. 7 is an assembled view of the platform and sample processing device of FIG. 6.

Turning now to FIGS. 6 and 7, where an alternative apparatus according to the present invention is depicted. The depicted apparatus is useful in those systems and methods in which vacuum is used to remove the processed sample materials from the platform 120. The apparatus includes a platform 120, a vacuum manifold collar 150, and a manifold base 170 in between which a standard microtiter plate 160 is located when the collar 150 and base 170 are assembled. Together, the vacuum manifold collar 150 and manifold base 170 provide a vacuum manifold useful in extracting sample material from the platform 120 and transferring it to the microtiter plate 160 for processing using conventional processes and equipment.

The platform 120 includes retention structure 122 similar to that described with respect to platform 20 above. A spindle opening 123 is included within the retention structure 122 to receive a spindle adapted to rotate a processing device located therein (not shown).

The platform 120 also includes optional sample fluid chambers 124 that may be used as a staging area for samples to be introduced onto a processing device. The fluid chambers 124 may also contain one or more reagents. The fluid chambers 124 may preferably be arranged in a rectilinear array that is similar in form to arrays of wells on a standard microtiter plate.

The platform 120 also includes stationary fluid chambers 126 to be used to receive processed sample material removed from a processing device. The fluid chambers 126 may include filter material. The fluid chambers 126 on the platform 120 may preferably be arranged in a rectilinear array that is similar in form to arrays of wells found on standard microtiter plates.

Further, the fluid chambers 126 are also preferably spaced at intervals compatible with the spacing of the wells 162 on the microtiter plate 160 such that each of the fluid chambers 126 is located above one of the wells 162 in the microtiter plate 160. It may be preferred that the fluid chambers 126 include extended drain ports 128 adapted to extend at least partially into the microtiter plate wells 162. The extended drain ports 128 may assist in preventing cross-contamination during the transfer of materials from the fluid chambers 126 on the platform 120 to the microtiter plate wells 162.

The vacuum manifold collar 150 preferably includes a seat 152 adapted to receive the lower surface of platform 120. A gasket 156 may preferably be located within the seat 152 to assist in sealing around the lower surface of platform 120 when a vacuum is supplied to the manifold. The collar 150 also includes an opening 154 through which the extended drain ports 128 on the fluid chambers 126 extend when the apparatus is assembled. The manifold base 170 may also preferably include a gasket 172 to assist in sealing the manifold collar 150 to the manifold base 170.

During use, a vacuum source may be connected to the assembled manifold base 170 and collar 150 to provide a negative pressure that draws processed sample material in the fluid chambers 126 into the microtiter plate wells 162. If the fluid chambers 126 contain filter material, then the processed sample materials in the fluid chambers 126 may be filtered during transfer to the microtiter plate 160. After the transfer is completed, the microtiter plate 160 can be removed and processed using conventional methods and techniques.

One alternative to the use of vacuum in connection with the apparatus depicted in FIGS. 6 and 7 is the use of positive pressure from above the fluid chambers 126 to fore the sample materials in the fluid chambers down through the drain ports 128 and into the microtiter plat 160. In such an apparatus, it may be necessary to provide a pressure manifold that seals about the top surface of the platform 120 around the openings of the fluid chambers 126.

Patents, patent applications, and publications disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. An apparatus for processing sample materials, the apparatus comprising:

a platform comprising an upper surface and a lower surface;

a plurality of stationary fluid chambers opening at the upper surface of the platform;

retention structure occupying a portion of the upper surface of the platform, wherein the retention structure is capable of retaining a rotating multi-chambered processing device proximate the upper surface of the platform, and wherein at least some of the plurality of stationary fluid chambers further comprise filter material.

2. An apparatus according to claim 1, wherein the fluid chambers comprising filter material further comprise a drain port opening at the lower surface of the platform.

3. An apparatus according to claim 2, wherein each of the drain ports comprises a drain extension.

4. An apparatus for processing sample materials, the apparatus comprising:

a platform comprising an upper surface and a lower surface;

a plurality of stationary fluid chambers opening at the upper surface of the platform, wherein the plurality of stationary fluid chambers are arranged in a rectilinear array on the upper surface of the platform;

retention structure occupying a portion of the upper surge of the platform; and a processing device located within the retention structure proximate the upper surface of the platform, the processing device comprising a plurality of process chambers, wherein the processing device is capable of being rotated within the retention structure to move the plurality process chambers, and wherein at least one of the process chambers on the processing device is positioned at a transfer site proximate the upper surface of the platform, wherein the location of the transfer site is fixed relative to the stationary fluid chambers, and further comprising complementary registration structure on the platform and the processing device, the complementary registration structure aligning the at least one process chamber at the location defined by the rectilinear array of the stationary fluid chamber when the processing device is stationary.

5. An apparatus for processing sample materials, the apparatus comprising:

a platform comprising an upper surface and a lower surface;

a plurality of stationary fluid chambers opening at the upper surface of the platform, wherein at least some of the plurality of stationary fluid chambers further comprise filter material;

retention structure occupying a portion of the upper surface of the platform; and a processing device located within the retention structure proximate the upper surface of the platform, the processing device comprising a plurality of process chambers, wherein the processing device is capable of being rotated within the retention structure to move the plurality process chambers.

6. An apparatus according to claim 5, wherein the fluid chambers comprising filter material further comprise a drain port opening at the lower surface of the platform.

7. An apparatus according to claim 6, wherein each of the ports comprises a drain extension.

8. An apparatus according to claim 6, further comprising a vacuum manifold.

9. An apparatus for processing sample materials, the apparatus comprising:

a platform comprising an upper surface and a lower surface;

a plurality of stationary fluid chambers opening at the upper surface of the platform;

retention structure occupying a portion of the upper surface of the platform; and a processing device located within the retention structure proximate the upper surface of the platform, the processing device comprising a plurality of process chambers, wherein the processing device is capable of being rotated within the retention structure to move the plurality of process chambers, and wherein the processing device is captive within the retention structure on the platform.

10. A method of processing sample material, the method comprising:

providing a platform comprising an upper surface and a lower surface, a plurality of stationary fluid chambers opening at the upper surface of the platform, and retention structure occupying a portion of the upper surface of the platform;

providing a processing device in the retention structure proximate the upper surface of the platform, the processing device comprising a plurality of process chambers;

providing sample material in a plurality of the plurality of process chambers on the processing device;

delivering energy to the process chambers containing sample material to raise the temperature of the sample materials in the process chambers; and rotating the processing device about an axis of rotation within the retention structure while delivering the energy, wherein the temperature of the sample materials in the process chambers is controlled as the processing device rotates to process the sample materials.

11. A method according to claim 10, wherein the energy comprises electromagnetic energy.

12. A method according to claim 10, wherein rotating the processing device comprises extending a spindle through a spindle opening formed through the upper and lower surfaces of the platform, the spindle opening located within the retention structure, and rotating the processing device using the spindle.

13. A method according to claim 10, further comprising transferring the sample materials from the process chambers on the processing device to the plurality of stationary fluid chambers on the platform after processing the sample materials.

14. A method according to claim 13, wherein the fluid chambers comprise filter material.

15. A method according to claim 13, further comprising transferring the sample material from the fluid chambers of the platform to a microliter plate comprising a plurality of wells.

16. A method according to claim 15, wherein transferring the sample materials comprises passing the sample materials in the fluid chambers through drain ports opening at the lower surface of the platform.

17. A method according to claim 16, wherein the fluid chambers comprise filter material, and further wherein passing the sample material through the drain ports comprises passing the sample materials through the filter material in the fluid chambers.

18. A method according to claim 16, wherein the passing of sample material through the drain ports is accomplished using vacuum.

19. A method according to claim 18, wherein the vacuum is delivered by placing the lower surface of the platform on a vacuum manifold and drawing a vacuum between the platform and the vacuum manifold.

20. A method according to claim 10, wherein the plurality of stationary fluid chambers on the platform are arranged in a rectilinear array on the upper surface of the platform.

21. A method according to claim 20, further comprising positioning at least one of the process chains on the processing device at a transfer site proximate the upper surface of the platform, wherein the location of the transfer site is fixed relative to the stationary fluid chambers.

22. A method according to claim 21, further comprising transferring the sample material from the process chamber located at the transfer site to one of the stationary fluid chambers on the platform after processing the sample materials.

23. A method according to claim 21, wherein the positioning further comprises providing complementary registration structure on the platform and the processing device, the complementary registration structure aligning the at least one process chamber at the transfer site when the processing device is stationary.

24. A method of processing sample material, the method comprising:
provproviding a platform comprising an upper surface and a lower surface, a plurality of stationary fluid chambers opening at the upper surface of the platform, and retention structure occupying a portion of the upper surface of the platform, wherein the plurality of stationary fluid chambers are arranged in a rectilinear array on the upper surface of the platform;
placing a processing device in the retention stricture proximate the upper surface of the platform, the processing device comprising a plurality of process chambers;
positioning at least one of the process chambers on the processing device at a transfer site proximate the upper suite of the platform, wherein the location of the transfer site is fixed relative to the stationary fluid chambers;
loading sample material in a plurality of the plurality of process chambers on the processing device, wherein the process chamber are loaded while positioned at the transfer site;
rotating the processing device about an axis of rotation within the retention structure on a spindle extending through a spindle opening formed through the upper and lower surfaces of the platform;
delivering energy to at least some of the plurality of process chambers containing sample material while rotating the processing device to control the temperature of the sample materials in the process chambers, whereby the sample materials am processed; and
transferring the sample materials from the process chambers on the processing device to the plurality of stationary fluid chambers on the platform after processing the sample materials; where the sample materials in the process chamber are transferred while the process chambers are located at the transfer site.

25. A method according to claim 24, wherein the energy comprises electromagnetic energy.

26. A method according to claim 24, wherein the fluid chambers comprise filter material.

27. A method according to claim 26, further comprising transferring the sample material from the stationary fluid chambers of the platform to a microtiter plate comprising a plurality of wells.

28. A method according to claim 27, wherein the transferring of sample materials from the stationary fluid chambers comprises passing the sample materials in the fluid chambers through drain ports opening at the lower surface of the platform.

29. A method according to claim 28, wherein the fluid chambers comprise filter material, and farther wherein passing the sample material through the drain ports comprises passing the sample materials through the filter material in the fluid chambers.

30. A method according to claim 28, wherein the passing of sample material through the drain ports is accomplished using vacuum.

31. A method according to claim 30, wherein the vacuum is delivered by placing the lower surface of the platform on a vacuum manifold and drawing a vacuum between the platform and the vacuum manifold.

32. A method according to claim 24, wherein the positioning further comprises providing complementary registration structure on the platform and the processing device, the complementary registration structure aligning the at least one process chamber at the transfer site when the processing device is stationary.

33. A system for processing sample material, the system comprising:
a workspace comprising a processing station;
at least one platform located within the workspace, each platform comprising an upper surface and a lower surface, a plurality of stationary fluid chambers opening at the upper surface of the platform, and retention structure occupying a portion of the upper surface of the platform;
at least one processing device located within the workspace, each processing device comprising a plurality of process chambers, wherein rotation of the processing device within the retention structure on the platform moves the plurality of process chambers in a circular pattern;
a spindle located at the processing station; and
a transfer device operative within the workspace, the transfer device capable of erring sample material from the processing station to another location within the workspace.

34. A system according to claim 33, wherein the workspace further comprises an unloading station, and further wherein the transfer device transfers sample material by transferring the at least one platform from the processing station to the unloading station.

35. A system according to claim 33, wherein the transfer device is capable of transferring sample material from the at least one processing device to the stationary fluid chambers of the at least one platform.

36. A system according to claim 33, further comprising a plurality of processing devices located within the workspace.

37. A system according to claim 33, further comprising a plurality of platforms located within the workspace.

38. A system according to claim 33, wherein the at least one platform further comprises a spindle opening formed through the upper and lower surfaces of the platform, the spindle opening located within the retention structure, whereby a spindle is capable of contacting and rotating the processing device proximate the upper surface of the platform when the platform and the processing device are located at the processing station.

* * * * *

UNITED STATES PATENT AND TRADEMARK OFFICE
CERTIFICATE OF CORRECTION

PATENT NO. : 6,855,553 B1
DATED : February 15, 2005
INVENTOR(S) : Bedingham, William It is certified that error appears in the above-identified patent and that said Letters Patent is hereby corrected as shown below:

Column 1,
Line 22, delete "les" and insert in place thereof -- samples --.
Line 64, delete the word "my" and insert in place thereof -- may be --.
Line 65, delete the word "microliter" and insert in place thereof -- microtiter --.

Column 6,
Line 23, delete the word "tided" and insert in place thereof -- titled --.

Column 8,
Line 31, delete the word "fore" and insert in place thereof -- force --.

Column 9,
Line 7, delete the word "surge" and insert in place thereof -- surface --.
Line 24, delete the word "chamber" and insert in place thereof -- chambers --.
Line 46, insert -- drain -- before "ports".

Column 10,
Line 37, delete the word "microliter" and insert in place thereof -- microtiter --.
Line 59, delete the word "chains" and insert in place thereof -- chambers --.

Column 11,
Line 16, delete the word "stricture" and insert in place thereof -- structure --.
Line 23, delete the word "suite" and insert in place thereof -- surface --.
Line 28, delete the word "chamber" and insert in place thereof -- chambers --.
Line 38, delete the word "am" and insert in place thereof -- are --.
Line 43, delete the word "chamber" and insert in place thereof -- chambers --.
Line 59, delete the word "farther" and insert in place thereof -- further --.

UNITED STATES PATENT AND TRADEMARK OFFICE
CERTIFICATE OF CORRECTION

PATENT NO. : 6,855,553 B1
DATED : February 15, 2005
INVENTOR(S) : Bedingham, William It is certified that error appears in the above-identified patent and that said Letters Patent is hereby corrected as shown below:

Column 12,
Line 34, delete the word "erring" and insert in place thereof -- transferring --.

Signed and Sealed this

Seventeenth Day of May, 2005

JON W. DUDAS
*Director of the United States Patent and Trademark Office*